United States Patent
Harkness (10) Patent No.: US 9,666,091 B2
(45) Date of Patent: May 30, 2017

(54) DRIVER TRAINING SYSTEM

(75) Inventor: Richard Harkness, Sacramento, CA (US)

(73) Assignee: LIFELONG DRIVER LLC, Incline Village, NV (US)

( * ) Notice: Subject to any disclaimer, the term of this patent is extended or adjusted under 35 U.S.C. 154(b) by 1186 days.

(21) Appl. No.: 11/972,512

(22) Filed: Jan. 10, 2008

(65) Prior Publication Data

US 2009/0181349 A1    Jul. 16, 2009

(51) Int. Cl.
| | | |
|---|---|---|
| G09B 9/04 | (2006.01) |
| G09B 9/052 | (2006.01) |
| A61B 3/032 | (2006.01) |
| A61B 5/16 | (2006.01) |
| G09B 19/16 | (2006.01) |
| G09B 9/05 | (2006.01) |

(52) U.S. Cl.
CPC ............... *G09B 9/04* (2013.01); *G09B 9/052* (2013.01); *A61B 3/032* (2013.01); *A61B 5/16* (2013.01); *A61B 5/162* (2013.01); *A61B 2505/09* (2013.01); *G09B 9/05* (2013.01); *G09B 19/167* (2013.01)

(58) Field of Classification Search
CPC ........... A61B 5/16; A61B 3/032; A61B 5/162; A61B 2505/09; A61B 5/18; A61B 3/00; G09B 7/00; G09B 19/167; G09B 9/05; G09B 9/04; G09B 9/052; G09B 5/02; G09B 9/10
USPC ........ 434/69, 236, 64, 65, 62; 340/576, 435; 600/300; 703/6
See application file for complete search history.

(56) References Cited

U.S. PATENT DOCUMENTS

| | | |
|---|---|---|
| 3,777,413 A | 12/1973 | Zaccheo |
| 3,916,534 A | 11/1975 | Riccio |
| 4,486,180 A | 12/1984 | Riley |
| 4,500,868 A | 2/1985 | Tokitsu et al. |
| 4,750,888 A | 6/1988 | Allard et al. |

(Continued)

OTHER PUBLICATIONS

Alexander Pollatsek, Vinod Narayanaan, Anuj Pradhan, and Donald L. Fisher, "Using Eye Movements to Evaluate a PC-Based Risk Awareness and Perception Training Program on a Driving Simulator", Fall 2006, Human Factors, vol. 48, No. 3, pp. 447-464.*

(Continued)

*Primary Examiner* — Jack Yip
(74) *Attorney, Agent, or Firm* — Amin, Turocy & Watson, LLP (57) ABSTRACT

The invention provides a computerized assessment system, as well as a method, that can be used for diagnosing driving skills in a driver of the class of vehicle drivers having impaired abilities. The system utilizes a) at least one prerecorded audio/visual training session capable of diagnosing the visual cognition, visual memory and visual recall abilities of a motor vehicle driver, where the training session comprises interactive driving simulations presented through four active visual zones; b) computerized means for digitally assessing driver actions in response to simulated driving situations presented by the interactive driving simulations; c) a database that records the driver actions; and d) a computer program capable of developing a diagnostic assessment of the visual cognition, visual memory and visual recall abilities of the driver.

14 Claims, 2 Drawing Sheets

(56) References Cited

U.S. PATENT DOCUMENTS

| | | | |
|---|---|---|---|
| 4,814,896 A | 3/1989 | Heitzman et al. | |
| 4,846,686 A | 7/1989 | Adams | |
| 4,868,771 A | 9/1989 | Quick et al. | |
| 4,939,587 A | 7/1990 | Deslypper | |
| 4,952,152 A | 8/1990 | Briggs et al. | |
| 5,131,848 A | 7/1992 | Adams | |
| 5,184,956 A | 2/1993 | Langlais et al. | |
| 5,187,571 A | 2/1993 | Braun et al. | |
| 5,209,662 A | 5/1993 | Fujita et al. | |
| 5,253,107 A | 10/1993 | Smith | |
| 5,275,565 A | 1/1994 | Moncrief | |
| 5,344,324 A | 9/1994 | O'Donnell et al. | |
| 5,350,179 A | 9/1994 | Hill et al. | |
| 5,366,376 A | 11/1994 | Copperman et al. | |
| 5,474,453 A | 12/1995 | Copperman | |
| 5,486,112 A | 1/1996 | Troudet et al. | |
| 5,499,182 A | 3/1996 | Ousborne | |
| 5,613,032 A | 3/1997 | Cruz et al. | |
| 5,652,717 A | 7/1997 | Miller et al. | |
| 5,660,547 A | 8/1997 | Copperman | |
| 5,807,114 A | 9/1998 | Hodges et al. | |
| 5,813,863 A | 9/1998 | Sloane et al. | |
| 5,828,943 A | 10/1998 | Brown | |
| 5,888,074 A | 3/1999 | Staplin et al. | |
| 5,919,046 A | 7/1999 | Hull | |
| 5,954,510 A | 9/1999 | Merrill et al. | |
| 6,227,862 B1 | 5/2001 | Harkness | |
| 6,632,174 B1* | 10/2003 | Breznitz | 600/300 |
| 6,927,694 B1* | 8/2005 | Smith et al. | 340/576 |
| 8,323,025 B2 | 12/2012 | Freund et al. | |
| 8,576,286 B1 | 11/2013 | Childs | |
| 8,598,977 B2 | 12/2013 | Maalouf et al. | |
| 2007/0015117 A1 | 1/2007 | Freund et al. | |
| 2007/0072154 A1 | 3/2007 | Akatsuka et al. | |
| 2007/0081262 A1 | 4/2007 | Oizumi | |
| 2008/0108022 A1* | 5/2008 | Freund | 434/69 |
| 2009/0011389 A1 | 1/2009 | Sizov | |
| 2009/0181349 A1 | 7/2009 | Harkness | |
| 2011/0076650 A1 | 3/2011 | Best | |
| 2014/0220513 A1 | 8/2014 | Harkness | |

OTHER PUBLICATIONS

Notice of Allowance for U.S. Appl. No. 13/286,210, dated Jan. 13, 2016, 28 pages.

Office Action for U.S. Appl. No. 15/096,959, dated Jun. 1, 2016, 24 pages.

Notice of Allowance for U.S. Appl. No. 15/096,959, dated Jul. 20, 2016, 21 pages.

Office Action for U.S. Appl. No. 14/563,182, dated Aug. 19, 2016, 29 pages.

Defensive Driving Strategies [online]. [retrieved on Aug. 8, 2016]. Retrieved from the Internet: URL: http://web.archive.org/web/20040804230200/http://www.webtrafficschool.com/wts/content!Florida/DefensiveDriving_Strategies.html (webtrafficschool.com) Published Aug. 4, 2004.

"How is teenSMART Different?" teenSMART, http://www.teensmartdriving.com/how/, Available May 9, 2014, 3 pages.

"teenSMART," ADEPT Driver, http://www.adeptdriver.com/products/teensmart/, Available May 9, 2014, 3 pages.

"What makes teenSMART successful?" teenSMART, http://www.teensmartdriving.com/what/, Available May 9, 2014, 3 pages.

"Why be a teenSMART Driver?" teenSMART, http://www.teensmartdriving.com/why/, Available May 9, 2014, 2 pages.

Berry, B., "ADEPT Driver Launches New Version of teenSMART to Kick Off National Distracted Driving Awareness Month," www.adeptdriver.com, Apr. 10, 2014, 2 pages.

International Search Report & Written Opinion for International Patent Application Serial No. PCT/US09/30765, dated Apr. 30, 2009, 6 pages.

Office Action for U.S. Appl. No. 13/286,210, dated Nov. 19, 2014, 17 pages.

Office Action for U.S. Appl. No. 14/563,182, dated Apr. 9, 2015, 16 pages.

Office Action for U.S. Appl. No. 14/563,182, dated Jul. 8, 2015, 15 pages.

Office Action for U.S. Appl. No. 13/286,210, dated Jul. 23, 2015, 24 pages.

\* cited by examiner

FIGURE 1

DRIVER TRAINING SYSTEM

BACKGROUND OF THE INVENTION

1. Field of the Invention

The present invention relates to systems and methods for assessing and training automobile drivers, and in particular, driver with potential driving impairments.

2. Description of Related Art

Various techniques, systems and methods are available for providing driver education and training. Most driver training systems and methods employ actual, behind the wheel driver training as at least one component. Such driver training may or may not be supplemented with classroom instruction.

Also known are driving simulators in which images are displayed on a display device. In such simulators a steering wheel, brake and accelerator are typically connected in a feedback loop and under computer control the image displayed varies as a function of the driver's operation those components. Additional views, such as left side views, right side views and rear views may be provided within separate windows on the display device, or using separate display devices for views in addition to views simulating a forward view.

U.S. Pat. No. 6,227,862, Harkness, May 8, 2001, discloses a system and method for providing driver training and also education focused on various areas that address driving and lifestyle skills. The six areas addressed are i) lifestyle, ii) risk and benefit perception, iii) visual search, iv) speed adjustment, v) space management and vi) hazard recognition. This system is designed to address the driver training needs of teen drivers, the population of drivers having the highest accident rate in the United States.

Driving ability is also a critical issue for senior drivers and other drivers experiencing a loss of or impairment in their driving skills, though the issues relating to senior driving have many societal implications for an aging population such as exists in the United States and many other industrialized nations.

Elderly people have higher rates of fatal crashes per mile driven, per 100,000 people, and per licensed driver than any other group, except young drivers. A problem is that elderly drivers don't deal as well as younger ones with complex traffic situations, and multiple-vehicle crashes at intersections increase markedly with age. Elderly drivers are more likely to get traffic citations for failing to yield, turning improperly, and running stop signs and red lights.

These issues are present in the elderly because of various impairments to driving ability. Visual acuity is the most obvious area of concern in this regard. Elderly drivers may experience impairments to their vision, from medical causes such as cataracts, glaucoma, or simply accentuated levels of near- or far-sightedness. Even where vision is normal, or can be corrected to normal, a senior may have lost some contrast sensitivity (the ability to detect sharp borders or slight changes in lighting), which is also critical to driving, particularly to driving at night.

Hearing loss among elderly drivers is another common physical impairment to driving, making the driver less likely to hear important auditory cues to driving, such as traffic noises, sirens, honking horns and the like. This is compounded in situations where drivers may be unaware of the loss of hearing.

Another potential impairment to driving ability in the elderly is the loss of range of motion. Arthritis, muscle degeneration, Parkinson's disease, and other health problems can decrease the older driver's ability to perform all the movements of driving and to respond quickly to emergencies. A driver may notice slower response to unexpected situations, such as trouble moving foot from gas to brake pedal or confusing the two pedals. For some drivers, it becomes harder to turn around to check over shoulder while backing up or changing lanes.

In some cases, the elderly driver may reach a stage where he or she is easily distracted or finds it hard to concentrate while driving. Many medications that are more commonly used by the elderly will affect the driver in such ways. These affects are highly variable from person to person, however, and may depend on the use of other medications, or general physical condition.

Car accidents are also more dangerous for seniors than for younger people, and a frail driver is more likely to be seriously hurt, more likely to require hospitalization, and more likely to die than a younger person involved in a similar car accident. Elderly people are not only more susceptible than younger people to medical complications following motor vehicle crash injuries, they are also more likely to die from their injuries. Based on the U.S. Department of Transportation's Fatality Analysis Reporting System, people 65 years and older represented 13 percent of the population in 1996 and 17 percent of motor vehicle deaths.

While safe driving is an important issue, everyone ages differently, and some people are able to retain a high level of driving ability into their seventies and eighties. The independence provided by driving is a valued element of the perception of quality of life for many seniors. Many seniors will view any loss of driving privileges as a loss of freedom. In many families, the decision to restrict the driving of an elderly family member is very difficult. In some cases it may be necessary to involve the driver's doctor as a trusted person for providing impartial advice on health issues that may affect driving. However, there is sometimes little or no motivation for an older existing driver to learn new safety skills, unless the decline in there abilities can be documented for them. Thus, while certain safety skills may be taught to improve the ability of the senior driver, there must be a recognition by the driver of what his diminished abilities are.

Presently, where a driver faces some physical or other impairment, a third party may be required to help assess the drivers driving ability, for instance, by testing vision, reflexes, strength, attention, and other factors. In the case of seniors, recommendations to the driver or the driver's family member are often made regarding placing restrictions or limitations on the driver's actions, or, deciding to stop driving altogether. In a commercial setting a visual cognition impairment observed in an employee driver may give rise to concern and the need for assessment as part of controlling liability.

Alternatively, in many states the Department of Motor Vehicles, Veterans Administration, or other vocational or rehabilitation center might be contacted. All of these options can be intimidating and threatening, particularly to a senior driver already facing concerns about frailty or diminishing cognitive abilities, and the driver may thus be reluctant to undertake such a visit for fear that their driving privileges could be removed.

Some seniors, alternatively, are aware of their own aging process, and may become nervous or tentative in driving. Many seniors give up driving voluntarily, perhaps unnecessarily. When a senior stops driving, this may presents a situation where an additional burden is placed on family or caregivers, as the senior is no longer able to conduct the normal chores of modern living, like visiting friends, shopping or attending various appointments. In such situations, it may be desirable to keep the senior driving, if this can be done under the safest possible, even if somewhat restricted, situations. Restrictions may be to limit driving to certain times of day or to driving only in familiar areas. The motivation of the senior driver to remain driving may again depend on some documented information regarding the extent of their remaining abilities.

The fact of the gradual impairment in driving ability with age, and that some elders become a high risk for road accidents, also creates a problem for policy planners, who must balance the social costs and benefits of senior driving. With the aging of the baby boomers, and the increasing life expectancy, aging drivers will become an issue of greater and greater concern to society. Persons 65 years old and older make up 13 percent of the population. The states with the highest percentage of older persons are Florida, 18 percent; Pennsylvania, 16 percent; Rhode Island, 16 percent; West Virginia, 15 percent; and Iowa, 15 percent. States with the lowest percentage of older persons are: Alaska, 5 percent; Utah, 9 percent; Texas, 10 percent; Georgia, 10 percent; Colorado, 10 percent. By 2030, elderly people are expected to represent 20 percent of the population in the United States.

Some communities provide alternatives to driving for seniors, inexpensive shuttles or buses, taxi vouchers, etc., but these all come at a cost, either to the individual or to the community. In some states the Department of Motor Vehicles have developed programs to evaluate individual driving abilities or may offer special licensing alternatives.

A further cost is the cost of insuring senior drivers. As they are subject to more accidents, the rates for insuring senior drivers will naturally be increased as they age. A blanket policy, however, fails to distinguish among the truly impaired drivers and those that may be driving safely into their eighties. One solution is to regularly test senior drivers, or require that at certain stages they take a refresher driving course, possibly a course tailored to the issues and concerns of elderly drivers. Regular check-ups for hearing, vision and general health, when reported to the insurance company, can provide some basis for continued insurability.

Policies can also be adjusted to reflect these concerns. AAA encourages every state to have a medical advisory or review board comprised of physicians and health care professionals to assess driver capabilities. AAA's Basic Best Practices recommends that these boards develop medical guidelines for licensing in the state and that they be given the authority to recommend customized or restricted licenses that allow driving privileges under certain conditions.

As an alternative, these individuals can contact a local driving school to assess his or her skills. The AARP has a Driver Safety Program taught as a classroom course designed for older drivers to help them hone their skills and avoid accidents and traffic violations. Website features information on the classess and on senior driving in general, including FAQs, a driving IQ test, a close call test, and directions to a driving course nearby.

Physicians can also refer people with mild cognitive problems to a hospital or rehabilitation facility with a driver evaluation program. The individual will then go through a series of tests to measure critical driving skills. The "Physician's Guide to Assessing and Counseling Older Drivers", developed by the American Medical Association in cooperation with the National Highway Traffic Safety Administration, assists physicians in evaluating the ability of their older patients to operate a motor vehicle safely. This 226-page guide includes checklists for vision and motor skills.

However, notwithstanding such training and education opportunities, over the years there have been no significant advances in the ability to monitor the declining driving abilities of existing drivers. It would be desirable to be able to easily and quickly assess the decline in certain motor skill and cognitive abilities of senior drivers, and to use that assessment in designing a program for assisting the individual senior in overcoming their particular areas of impairment, and thus improving their driving abilities. It is believed that newer techniques are necessary to screen such drivers, and to provide a mechanism to train drivers with declining skills to learn newer or adaptive strategies tailored to their remaining abilities that will result in reductions in accident rates.

SUMMARY OF THE INVENTION

A system and method are disclosed for diagnosing driving skills in a motor vehicle driver, or driver, of the class of drivers having impaired abilities.

The method comprises the steps of: a) presenting a motor vehicle driver with at least one prerecorded audio/visual training session capable of diagnosing visual cognition, visual memory and visual recall abilities of said driver, wherein said training session comprises interactive driving simulations presented through four active visual zones; b) digitally assessing driver actions in response to simulated driving situations presented by the interactive driving simulations; c) creating a database that records the driver actions; and d) developing a diagnostic assessment of the visual cognition, visual memory and visual recall abilities of the driver.

The system and method have particular relevance to drivers of commercial vehicles, or drivers of public safety vehicles, such as fireman, policemen or ambulance drivers, where a high level of driving skill and ability is demanded by the job.

In another preferred aspect, the system and method are applied to a driver having impaired abilities, for instances, as a consequence of a debilitating disease or condition, or as a consequence of aging.

In one preferred embodiment, the system further comprises in step b) digitally assessing the time of actions made in response to the simulated driving situations.

In a different aspect, the method according to the invention further comprises developing a training module of individualized and prescriptive instruction based on the diagnostic assessment and comprising at least one training lesson.

In another aspect, steps a) through d) are repeated to assess rehabilitation of the driver's visual cognition, visual memory and visual recall abilities in response to the prescriptive instruction.

In a preferred embodiment, information regarding the progress and results of the training module is provided to a the driver, for purposes of self-diagnosis and monitoring of the recovery of visual cognition abilities.

In another preferred embodiment of the invention, information regarding successful completion of the training module can be provided to a designated third party, as evidence of the rehabilitation of the drivers skills. In one such aspect of this embodiment, a third party is selected from the group consisting of an insurance agency, a state motor vehicle agency, a police department, an automotive association and a rehabilitation center.

In a further preferred embodiment, the third party is, for instance, an insurance company or agency that authorizes a discounted insurance rate for the driver in response to the evidence of rehabilitation.

Another preferred embodiment of the invention provides computer based training to supplement the audio/video presentation of a) in the areas of visual cognition, visual memory and visual recall.

The interactive driving simulations in a) are preferably presented using digital frame based technology.

In a different preferred embodiment of the invention the training sessions in step a) that are further designed to assess abilities relating to lateral search, risk perception, speed adjustment, space management, and hazard recognition.

In another preferred embodiment the four active visual zones in step b) comprise visual zones will correspond to the three active mirrors and windshield view of a four camera point of view driving simulation. In a further such preferred embodiment, in step b) the two inactive blind spots excluded from the four active visual zones are also assessed.

In a different preferred method according to the invention in step b) unobtrusive psychodiagnostics are employed in the diagnostic assessment.

The invention also provides a computerized assessment system utilizing a) at least one prerecorded audio/visual training session capable of diagnosing the visual cognition, visual memory and visual recall abilities of a motor vehicle driver, where the training session comprises interactive driving simulations presented through four active visual zones; b) computerized means for digitally assessing driver actions in response to simulated driving situations presented by the interactive driving simulations; c) a database that records the driver actions; and d) a computer program capable of developing a diagnostic assessment of the visual cognition, visual memory and visual recall abilities of the driver.

BRIEF DESCRIPTION OF THE DRAWINGS

Various exemplary embodiments of this invention will be described in detail, with reference to the following figures, wherein.

DETAILED DESCRIPTION OF THE PREFERRED EMBODIMENT

The present invention provides a system and method for providing driver training and education for drivers having impaired abilities relating to driving skills, such as the normal impairments in visual cognition and hazard detection attendant to aging.

In one aspect, the invention provides a psychometric instrument for measuring visual cognition, visual memory and visual recall in senior and other automobile drivers having impaired driving abilities, particularly in view of assessments made of the drivers reactions and response times to various driving simulations.

The invention further provides a tool for rehabilitation of drivers having impaired abilities. One feature is an training component adapted to address specific problems identified in the psychometric assessment. As part of an ongoing assessment, the methods can provide feedback for remediation. Further, certification provides additional incentive for learning new skills to compensate or overcome the impairments of the driver.

A visual cognition test involves full motion driving simulations to assess visual search skills. Visual memory and visual recall of the senior driver are also assessed. These are all timed to determine response speed. In a typical visual cognition test a driving simulation is played and then flashed to a graphic six zone screen that covers the driving scene. Then, the test taker is asked to point and click on the zone where a specific object was when the driving simulation stopped. This measures visual cognition, visual memory and visual recall all at once.

This test is used to diagnose visual impairment of drivers as well as to train drivers to improve their visual search skills.

The method also assesses hazard detection skills of the senior drivers. The typical hazard detection scenario is straight forward, where the test taker is presented a full motion driving scenario and clicks on to hazards as they appear during the driving scene. The test taker has to respond in a timely manner to get credit on hazard identification. In fact, this test measure response times of the test taker as part of the assessment, measured digitally and timed by the system apparatus. Reaction times are something particularly critical to assessing the abilities of senior drivers to the simulated driving situations.

The method and system employ and utilize various computerized means for presenting and recording the resulting actions of the driver. The system will include a computer program to present the at least one prerecorded audio/visual training session, with recording means for diagnosing the visual cognition, visual memory and visual recall abilities of a driver.

The four active visual zones will typically be presented to the driver by the use of computerized means for digitally assessing driver actions in response to simulated driving situations presented by the interactive driving simulations.

Figure 1:
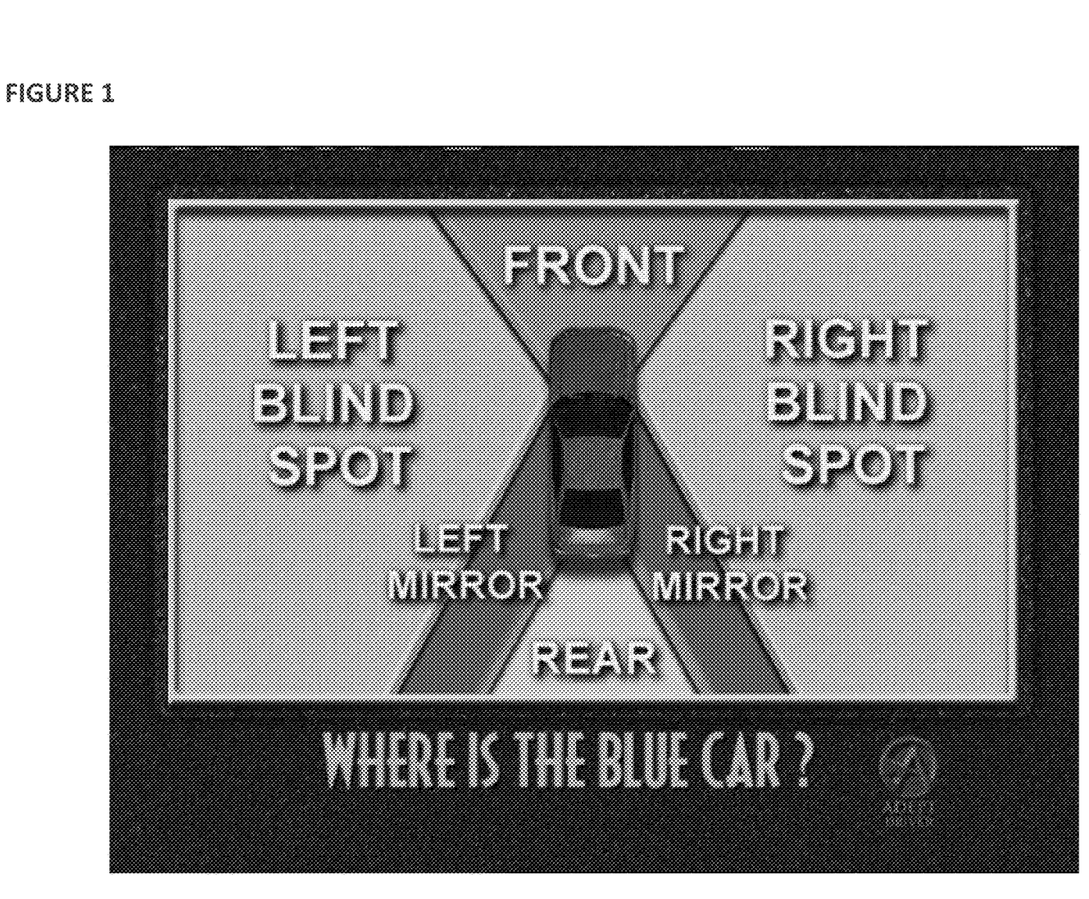
FIG. 1 is a diagram showing the views presented by the four camera field of view system (front zone, rear zone, left mirror zone, right mirror zone) utilized with computer based training.
Figure 2:
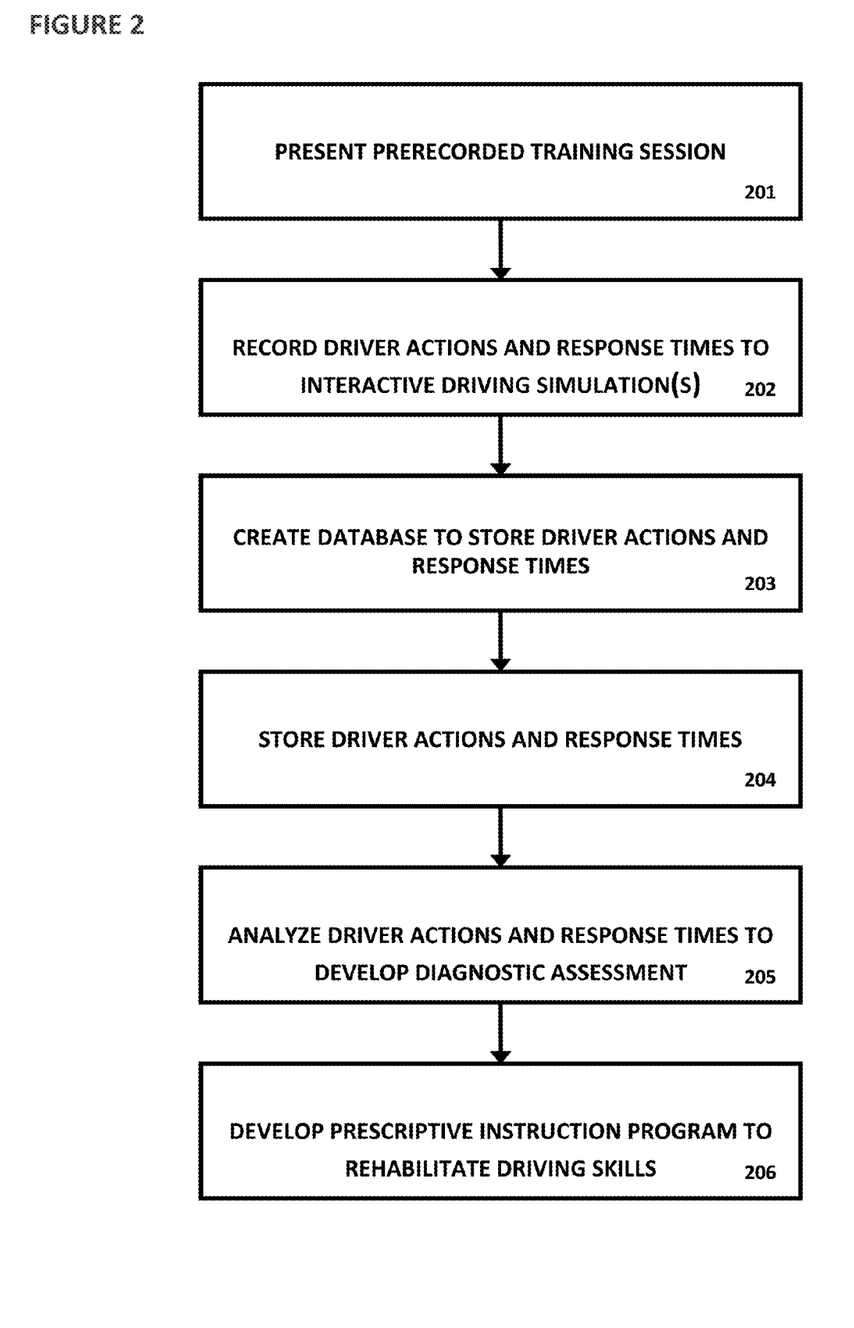

FIG. 1 shows the views presented by the four camera field of view system utilized with the CBT, a video-based system that uses custom computer software to execute and collect data as the driver progresses through the training or testing.

A driving scene is typically presented showing the four fields in a split screen system on a computer screen, which is then stopped before switching to a zone graphic with a question. The visible zones in the four camera field of view include the front zone, which includes everything visible through a windshield in driving, and occupies the full computer screen except the spaces reserved for the three small rectangular shaped images that appear to have a chrome border.

A left side mirror zone is provided in a chrome framed rectangular image in the lower left hand corner of the screen. The right side mirror zone is a chrome framed rectangular image in the lower right hand corner. A rear mirror zone is shown as a chrome framed rectangle in the upper center of the screen. Each mirror zone depicts its own scene recorded simultaneously with the main screen windshield view.

Further in reference to FIG. 1, the right blind spot zone is everything to the right of the car that can not bee seen in the front view, rear view or right side mirror zones. The left blind spot represents the zone to the left of the car that can not bee seen in the front view, rear view or left side mirror zones.

Objects are constantly moving in and out of these blind spots during the full motion video scenarios, just as in real world driving. The presentation of real world transitions among and between visible and blind spot zones permits a series of questions to be asked of the simulation driver. The driver at all times is expected to track and to know what is in the blind spots, and what is not there.

For example, if asked "Where is the white pickup truck now?" and the truck was slowly passing on the right and had just disappeared from the right rear mirror, the driver would respond; "in the right blind spot zone", even though the truck is not presently visible on the computer screen. Another possibility would be to ask the test taker "where is your escape path now?" If there had been no cars drifting in or out of the blind spot or right rear view mirror or ahead and immediately to the right then the driver could assume the right blind spot zone was clear and would most likely make for good escape path if needed at the moment.

The system may also be designed to assess the abilities of the driver relating to lateral search, risk perception, speed adjustment, space management, and hazard recognition.

As another feature of the method and system of driver assessment is the creation of a database that records driver actions. This database is used in developing a diagnostic assessment of the visual cognition, visual memory and visual recall abilities of the driver. Preferably, the system employs unobtrusive psychodiagnostic methods in the diagnostic assessment as part of the measurements taken of driver reactions and response times.

Another computer program is employed that is capable of developing a diagnostic assessment of the visual cognition, visual memory and visual recall abilities of the driver based on the recorded driver actions.

The use of digital frame based technology allows precise timing and very accurate comparisons of reactions that are made by the driver to the simulations presented by the system, and digital frame based technology is preferred for use with the system. Current digital camera and digital motion technologies are capable capturing a minimum of 720 by 485 pixels of data per frame, and at 30 frames per second. Alternatively, more traditional streaming video can be used with the system.

Based on the responses to the training sessions, a training module of individualized and prescriptive instruction is developed for a particular driver, based on the diagnostic assessment and comprising at least one training lesson. Lessons presented to individual drivers are designed to aid that particular driver in the strengthening of particular driver skills or, in some cases, the development compensating abilities for the deficiencies noted in the assessment. The training sessions may include computer based training to supplement the development of skills in the areas of visual cognition, visual memory and visual recall.

As one part of the prescriptive instruction, the driver may be asked to repeat the initial training session, in order to assess rehabilitation of the driver's visual cognition, visual memory and visual recall abilities.

Information regarding successful completion of the training module can be provided to a designated third party, as evidence of the rehabilitation of the drivers skills. In one such aspect of this embodiment, a third party is selected from the group consisting of an insurance agency, a state motor vehicle agency, a police department, an automotive association and a rehabilitation center. In a further preferred embodiment, the third party is, for instance, an insurance company or agency that authorizes a discounted insurance rate for the driver in response to the evidence of rehabilitation.

In one application of the system, the information from the assessment is directed to the drivers insurance company. In the latter regard, a certification program demonstrating the completion by the driver of the tailored training regimen can be used to provide information on the successful education of the impaired driver, with training of ways to compensate and drive safely in spite of certain impairments associated with aging.

Thus, even where a senior has failed to recognize his or her own declining abilities, or where the fear of giving up driving altogether makes the senior resistant to assessment in another setting, the system provides a safe and friendly assessment with the option of a training system to advance the driving abilities. Because the system offers diagnostic and specialized training, it is possible to offer the senior an option to become trained and more proficient, in compensating for the impairments of aging, and not necessarily have to fear a permanent loss of driving ability and subsequent dependence on others for the necessities of life, or loss of social and leisure activities The system is also suitable for the many elderly drivers that may wish to monitor themselves and gradually limit or stop driving as they feel certain driving situations have become safe. With computer based training (CBT) the assessment and training can be conducted on site, such as at a state motor vehicle department facility or physicians office, or the like, or accessed through the internet for home-based training. With home based training, interactive systems can be installed to monitor progress and report diagnostic test results to insurance agencies, motor vehicle departments, or other interested parties. With repeated tests, the improvement in driving abilities, or continued decline, can be monitored over time, so that both the extent of, and trend in, the impairment can be continuously assessed, and remedial actions taken as appropriate.

With the assessment and training method described herein, the question of whether and to what extent an impaired driver may be required give up the driving privilege can be answered privately, or only between the senior and limited family members or third parties of the seniors choosing.

Additionally, the system provides the opportunity for a training regimen tailored to the particular needs of a driver, and thus holds out the promise of eventual improvement and certification of safe driving skills. As one example, the National Highway Traffic Safety Administration suggests various ways that seniors can adapt to their changing abilities. If drivers often seem to suddenly stop in front of the senior, they are advised to pay extra attention to vehicles in front and maintain a safe distance between cars: one car length for every 10 miles per hour. If other drivers seem to be going especially fast to the senior, use the speed limit as a guide. The senior is urged to not feel pressured to drive unnecessarily fast, but to recognize that going too slowly can be just as dangerous. They are also urged to stay in the right-hand lane where they can.

If sharp turns are difficult for the senior to make, a recommendation is typically made to go as slowly as is needed and stay in the lane, using the signal and being sure it's off after completing the turn.

If highway driving gives the senior mote trouble than he or she is used to, the senior is asked to remember to stay in the lane that's going closest to their own speed, and keep up with the rest of traffic as best they can. Avoiding traveling during rush hour is also recommended.

These and other suggestions can aid the senior in driving safely with advancing age. However, the method described herein allows the rehabilitation and training that is very specifically targeted to that driver, with the aim of improving the seniors driving skills, particularly as regards to the skills involved in hazard detection and visual cognition. These skills can be trained, and are among the most likely skills to prevent accidents.

The following examples are representative of skills assessment for a senior driver, and diagnosis. Various changes can be made while not changing the basis of the assessment, with some adjustments being necessary for on-line or interactive internet applications of the driver assessment system.

Example I

Workout Session #1

A: Time: 60 minutes
B: Session Objectives:
To introduce the four camera point of view driving simulation system.
To introduce key facts about the issues of impairment in senior drivers
To distribute the "Program Materials" and provide a high-level overview of key program components
C: Instructional Elements/Sequence:
1. Warm-Up: Trigger Video: "Driving and the Aging Population" (2-3 minutes)
D: Description:
1. Warm-Up: Trigger Video: "Safe Driving for Seniors" (2-3 minutes): This introductory piece shows an overview of the program.
2. Trigger Video "Come One Let's Go" (2-3 minutes): In this video, a typical senior driving scenario is viewed to exemplify the introduced concepts.

Example II

Computer Familiarity and Self Assessment

A: Time: 60 minutes
B: Session Objectives:
To make the drivers comfortable interacting with the computer technology and provide them with an opportunity to navigate and practice.
To introduce concepts of driving introduced in the Orientation Video and Workout
To develop the driver's understanding of Visual Search techniques as the cornerstone of safe and skillful driving
To allow the driver to apply and practice Visual Search techniques in a variety of situations
To develop a database of senior responses for diagnostic and prescriptive study and remediation.
C: Instructional Elements/Sequence:
1. Logging On
2. CBT #0: Introduction: Preview and Practice (15 minutes)
3. CBT #1: "Driving With Your Eyes Wide Open" (15 minutes)
4. CBT #2: "Taking A Closer Look". (30 minutes)
D: Description:
1. Logging On
When the driver signs in and enters his/her password, he/she sees a Home Page that gives all the options. These include the following elements;
A CBT Practice option which can be accessed when the driver signs on; however, if this is the driver's first time. it will be highlighted with an "Intro" button A button which shows a "Run CBT" option which accesses the next CBT in the drivers progress path
Driver Status—shows which component has been completed
The CBTs that the driver has completed are "shaded out," the next available CBT highlighted—as the driver moves through the program
2. CBT Introduction: Preview and Practice (15 minutes)
(a) Purpose
The overall purpose of this CBT is to:
Give the drivers a chance to perform a brief "self-assessment" and complete a short survey of driving behaviors
Describe the various CBT components and basic CBT terminology
Give the drivers a chance to walk through driving scenarios
Build enthusiasm for the CBT approach
(b) Self-Assessment and Survey
The drivers are addressed directly throughout the CBTs. They are asked to do a self-assessment, asking some basic questions, such as:
On a scale of 1-10, how would you evaluate your own driving skills? (Seeing things around you in general? Spotting hazards/troubles before they happen? Adjusting your speed to the flow of traffic? Maintaining a safe distance? Handling risky situations?)
The drivers are then asked to complete survey questions about their driving behaviors. The responses are recorded in the database for future correlation analysis.
(c) Component Walk-Through
The CBT introduces each of the driving scenarios and allows the drivers to try each one:
Hazard Clicking which requires drivers to recognize and identify hazards by using the mouse to click on items they believe to meet the definition given in the instructions.
Driver Action which asks drivers to apply the appropriate responses (speed up, slow down, go left, go right) to various driving situations.
Where Is It? Drivers are asked to use visual search and recall skills to answer questions.
In each of the three types of driving scenarios, the driver's responses are recorded in the program database. The first response (first mouse click) to an exercise and in some cases, the last response is analyzed to identify response patterns at the conclusion of the program.

Example III

Rehabilitation

Once the driver has been assessed a program for prescriptive instruction is develop for the driver. This practice session/tutorial may model the driving practice sessions. The prescriptive instruction may include various elements, a few of which are summarized here.
1. "Driving With Your Eyes Wide Open" (15 minutes)
(a) Purpose
The overall purpose of this CBT is to:
Reinforce visual search as the bedrock component of visual cognition
Break down visual search into its components—search to front, back, sides
Provide elementary visual search practice
(b) Conceptual World View/Visual Search
The "film within a film" now picks up on the first day of shooting. The discussion regards the differences that occur in aging drivers abilities. The key point/question is now, "In which ways do various impairments to driver affect the ways they can anticipate and stay out of trouble?" The point comes out in the discussion that the failure to see other vehicles is the number one cause of accidents.

(c) Visual Search Components

This segues into a discussion of the various components of visual search. Illustration is provided in a simulated "drive" in the stage car (using rear screen projection) with a character in need of developing a refined driving skill set that makes compensation for the drivers impairments in visual cognition or hazard detection.

In the course of their drive, illustrative driving examples are provided for the following visual search techniques:
Search ahead, including concepts of:
Distance search
Visual lead time
Maintaining search ahead
Searching to the side, including:
Importance of lateral search techniques
What to look for at/how to handle controlled intersections
What to look for at/how to handle uncontrolled intersections In the course of their driving session, the actors reinforce a few ancillary points regarding safe and skillful driving.

(d) Visual Search Practice

The CBT concludes with a chance to practice the first element of visual search: search ahead. In doing so, the POV shifts so that it seems that the driver watching the CBT is getting behind the wheel.

The driver viewer is asked to identifying specific hazards in the environment. He/she does this in spite of possible distractions that might be closer to the driver. This leads to ideas about "distance searching" and not getting "locked in" to whatever is right in front of you. This exercise involves an element of timing that requires the driver to identify maneuvering and decision-making needs in advance in order to avoid last second reactions.

For example, the driver is asked to look ahead and move his/her mouse on to an oncoming potential hazard; e.g., pedestrians, car door opening, trucks unloading, cars pulling out. (Hazard Clicking.)

Each mouse click is recorded. When scored, as in the Certification Test, the number of correct responses is divided by the total possible hazards. This method evaluates performance in the hazard recognition domain. The immediate feedback lists the hazards missed for further emphasis during the next attempt.

2. "Visual memory and visual recall" (30 minutes)

(a) Purpose

The overall purpose of this CBT is to:

Allow the drivers to improve visual memory and visual recall.

(b) Visual Memory and Recall Practice

The first part of the exercise concentrates on mirror use and "search behind" techniques. In particular, it focuses on a series of exercises calling for using mirrors in conjunction to avoid accidents and "blind spots".

For example a "Where is it?" exercise shows a white van approaching fast in the rear view mirror, disappearing, appearing in the right hand mirror, and moving into the driver's blind spot. The video disappears and the six zone map pops up. The driver is asked "Where is it?" and to move his/her mouse and click on the zone area where the car is currently residing.

Subsequent exercises call for the driver to click the mouse on potential hazards as they move among all the mirrors.

While this invention has been described in conjunction with the specific embodiments outlined above, it is evident that many alternatives, modifications and variations will be apparent to those skilled in the art. Accordingly, the preferred embodiments of the invention, as set forth above, are intended to be illustrative, not limiting. Various changes may be made without departing from the spirit and scope of this invention.

What is claimed is:

1. A driving simulator for assessing and improving driving skills of a trainee having impaired driving abilities comprising:
a computerized audio/visual device programmed to:
display an interactive driving simulation presented through four active visual zones from a driver's-seat perspective comprising (1) a driver's forward view, (2) a rear mirror view, (3) a left side mirror view, and (4) a right side mirror view, wherein the rear mirror view, left side mirror view, and right side mirror view each simultaneously depict a scene occurring simultaneously with the driver's forward view;
display movement of an object moving through one of the four active visual zones and one of two inactive zones representing a left blind spot and a right blind spot;
track the location of the object in one of the four active visual zones or one of the two inactive zones;
stop the presentation of the training session after the object moves through at least two of the multiple active visual zones and one of the two inactive zones;
display a top-down-perspective graphic multi-zone screen, wherein each zone of the multi-zone screen represents one of the driver's forward view, the rear mirror view, the left side mirror view, the right side mirror view, the left blind spot, and the right blind spot respectively;
display a prompt to the trainee to point and click on the zone in the graphic multi-zone screen in which the object was located at the time the presentation of the training session was stopped;
receive the trainee's response to the prompt;
determine if the trainee's response to the prompt was correct; and
determine the trainee's response time to the prompt.

2. The driving simulator of claim 1 wherein the computerized audio/visual device is programmed to:
record whether the trainee response was correct;
record the trainee response time;
create a database for storing whether the trainee response was correct and the trainee response time;
store whether the trainee response was correct and the trainee response time; and
analyze whether the trainee response was correct and the trainee response time to develop a diagnostic assessment of impairments in the visual cognition, visual memory, and/or visual recall abilities of the trainee.

3. The driving-simulator of claim 1 wherein the multiple active visual zones of the training session are generated from a simultaneous four camera point of view recording.

4. The driving-simulator of claim 1 wherein the training session is presented using digital frame based technology.

5. The driving-simulator of claim 1 wherein the computerized audio/visual device is programmed to assess the trainee's lateral search, risk perception, speed adjustment, space management, and hazard recognition abilities based on whether the trainee response was correct and the trainee response time.

6. A computerized audio/visual driving simulator method for assessing and improving driving skills of a trainee having impaired driving abilities comprising:
 presenting to the trainee with the computerized audio/visual driving simulator an interactive driving simulation presented through four active visual zones from a driver's-seat perspective comprising (1) a driver's forward view, (2) a rear mirror view, (3) a left side mirror view, and (4) a right side mirror view, wherein the rear mirror view, left side mirror view, and right side mirror view each simultaneously depict a scene occurring simultaneously with the driver's forward view;
 displaying with the computerized audio/visual driving simulator movement of an object moving through one of the four active visual zones and one of two inactive zones representing a left blind spot and a right blind spot;
 tracking with the computerized audio/visual driving simulator the location of the object in one of the four active visual zones or one of the two inactive zones;
 stopping the presentation on the computerized audio/visual driving simulator of the training session after the object moves through at least two of the multiple active visual zones and one of the two inactive zones;
 displaying with the computerized audio/visual driving simulator a top-down-perspective graphic multi-zone screen, wherein each zone of the multi-zone screen represents one of the driver's forward view, the rear mirror view, the left side mirror view, the right side mirror view, the left blind spot, and the right blind spot respectively;
  displaying with the computerized audio/visual driving simulator a prompt to the trainee to point and click on the zone in the graphic multi-zone screen in which the object was located at the time the presentation of the training session was stopped;
  receiving with the computerized audio/visual driving simulator the trainee's response to the prompt; and
  determining with the computerized audio/visual driving simulator if the trainee's
   response to the prompt was correct and the trainee's response time to the prompt.

7. The method of claim 6 further comprising the steps of:
 recording with the computerized audio/visual driving simulator whether the trainee response was correct and the trainee response time;
 creating with the computerized audio/visual driving simulator a database for storing whether the trainee response was correct and the trainee response time;
 storing with the computerized audio/visual driving simulator whether the trainee response was correct and the trainee response time; and
 analyzing with the computerized audio/visual driving simulator whether the trainee's response was correct and the trainee's response time to develop a diagnostic assessment of impairments in the visual cognition, visual memory, and/or visual recall abilities of the trainee.

8. The method of claim 6 wherein the multiple active visual zones of the training session are generated from a simultaneous four camera point of view recording.

9. The method of claim 6 wherein the training session is presented using digital frame based technology.

10. The method of claim 6 comprising assessing with the computerized audio/visual driving simulator the trainee's lateral search, risk perception, speed adjustment, space management, and hazard recognition abilities based on whether the trainee response was correct and the trainee response time.

11. A computer-implemented method for assessing and improving driving skills of a trainee having impaired driving abilities comprising:
 presenting to the trainee an interactive driving simulation presented through four active visual zones from a driver's-seat perspective comprising (1) a driver's forward view, (2) a rear mirror view, (3) a left side mirror view, and (4) a right side mirror view, wherein the rear mirror view, left side mirror view, and right side mirror view each simultaneously depict a scene occurring simultaneously with the driver's forward view;
 displaying movement of an object moving through one of the four active visual zones and one of two inactive zones representing a left blind spot and a right blind spot;
 tracking the location of the object in one of the four active visual zones or one of the two inactive zones;
 stopping the presentation of the training session after the object moves through at least two of the multiple active visual zones and one of the two inactive zones;
 displaying a top-down-perspective graphic multi-zone screen, wherein each zone of the multi-zone screen represents one of the driver's forward view, the rear mirror view, the left side mirror view, the right side mirror view, the left blind spot, and the right blind spot respectively;
 displaying a prompt to the trainee to point and click on a the zone in the graphic multi-zone screen in which the object was located at the time the presentation of the training session was stopped;
 receiving the trainee's response to the prompt; and
 determining if the trainee's response to the prompt was correct and the trainee's response time to the prompt.

12. The method of claim 11 further comprising:
 recording whether the trainee response was correct and the trainee response time;
 creating a database for storing whether the trainee response was correct and the trainee response time;
 storing whether the trainee response was correct and the trainee response time; and
 analyzing whether the trainee's response was correct and the trainee's response time to develop a diagnostic assessment of impairments in the visual cognition, visual memory, and/or visual recall abilities of the trainee.

13. The method of claim 11 wherein the multiple active visual zones of the training session are generated from a simultaneous four camera point of view recording.

14. The method of claim 11 wherein the training session is presented using digital frame based technology.

* * * * *